United States Patent [19]

Nieves

[11] Patent Number: 5,261,531
[45] Date of Patent: Nov. 16, 1993

[54] FEMININE HYGIENE PACKAGE

[76] Inventor: Felipe A. Nieves, Urb. La Milagrosa - Jade St., F-31, Sabana Grande, P.R. 00637

[21] Appl. No.: 2,034

[22] Filed: Jan. 8, 1993

[51] Int. Cl.⁵ ............................................. B65D 77/06
[52] U.S. Cl. ................................. 206/205; 206/38; 206/581; 206/440; 206/459.5; 206/823
[58] Field of Search ................ 206/37, 38, 205, 210, 206/223, 235, 438, 459.5, 440, 581, 823

[56] References Cited

U.S. PATENT DOCUMENTS

| | | | |
|---|---|---|---|
| 2,623,566 | 12/1952 | Kibler | 206/581 |
| 2,764,201 | 9/1956 | Whippo | 206/581 |
| 3,557,853 | 1/1971 | Jones | |
| 4,286,639 | 9/1981 | Murphy | |
| 4,332,319 | 6/1982 | Hurwood | |
| 4,702,378 | 10/1987 | Finkel et al. | |
| 4,896,768 | 1/1990 | Anderson | |
| 4,901,851 | 2/1990 | Gerry | |
| 4,964,526 | 10/1990 | Stephens | 206/823 |
| 5,004,106 | 4/1991 | Blumstock et al. | 206/823 |

FOREIGN PATENT DOCUMENTS 2208986 8/1973 Fed. Rep. of Germany ... 206/459.5

*Primary Examiner*—Jimmy G. Foster
*Attorney, Agent, or Firm*—Richard C. Litman

[57] ABSTRACT

An inexpensive and compact sanitary kit for cleansing the body after discharge of bodily fluids. A dry wipe, an enclosed wet wipe, and a sanitary napkin are enclosed in an enclosure protecting the components during storage. The enclosure has length and width not exceeding 20 cm and 10 cm, respectively, and is usable in disposing of the wipes and of the napkin, if desired, after use.

2 Claims, 2 Drawing Sheets

FEMININE HYGIENE PACKAGE

BACKGROUND OF THE INVENTION

1. Field of the Invention

The present invention relates to a single use, disposable kit comprising certain specified components for women's hygienic care.

2. Description of the Prior Art

Problems inherent in coping with cleaning sudden or unexpected discharge of bodily fluids, as may occur with defecation of infants, menstruation of women, opening of wounds of injured persons, and similar events has led to many portable, convenient kits being proposed. Despite a superficial similarity of the above examples of distress which ordinarily require immediate, in situ clean up, each type of instance presents unique aspects of hygiene and practicality.

A comprehensive kit providing many items useful in the hygienic care of infants is seen in U.S. Pat. No. 4,702,378, issued to Henry Finkel et al. on Oct. 27, 1987. The kit disclosed therein includes wet and dry towels, baby powder, soap, a fresh diaper, and a coupon, all being contained within an envelope formed by a complicated folding scheme so as to house all kit components advantageously.

Less complicated kits are disclosed in U.S. Pat. Nos. 4,332,319, issued to David L. Hurwood on Jun. 1, 1982, and 4,901,851, issued to Martincic Gerry on Feb. 20, 1990. Hurwood provides a two receptacle packet separately enclosing a moist napkin and moisture absorbing powder. Gerry provides two separately enclosed sponges impregnated with water and soap, and water and fragrance, respectively.

U.S. Pat. No. 4,896,768, issued to Leslie B. Anderson on Jan. 30, 1990, discloses a prepackaged antibacterial and antiviral wipe.

U.S. Pat. Nos. 3,557,853, issued to Mary Henning Jones on Jan. 26, 1971, and 4,286,639, issued to Jeannie P. Murphy on Sep. 1, 1981, disclose holders for sanitary napkins. Murphy's invention provides a flat device similar to a wallet.

None of the above inventions and patents, taken either singly or in combination, is seen to describe the instant invention as claimed.

SUMMARY OF THE INVENTION

Onset of menstruation, or opening of an incision, and similar conditions may occur without warning and at unexpected times. It may be impossible to be prepared for this occurrence, and the sufferer may wish not to restrict his or her activities in anticipation thereof. It therefore becomes desirable to have a sanitary kit which provides wet and dry wiping objects for restoring the body area affected, and a sanitary napkin, bandage, or similar object for continuing protection after initial cleansing.

To be practical when carried about during diverse activities and given the varied nature of clothing worn when engaged in diverse activities, it is also desirable to form a sanitary kit to be as flat as is feasible. This enables the kit to be minimally obtrusive, even when carried in a small pocketbook, a garment having small pockets, and in other situations wherein little space is devoted to the sanitary kit.

The kit is preferably practical in its disposal after use. To this end, the envelope in which it is provided also serves as a disposal container.

Economics are also important, so that the sanitary kit is inexpensive to buy.

The sanitary kit of the present invention therefore provides a dry wiping object, a moistened wiping object sealed within its own wrapping, and a sanitary napkin also individually enclosed and sanitarily sealed. These components are provided in an enclosure of a light, thin, flexible plastic, which enclosure also serves as a disposal container.

Accordingly, it is a principal object of the invention to provide a sanitary kit including a moistened wiping object to facilitate initial cleansing, in which discharged bodily fluid is wiped from the skin or other body external surface, the moistened wiping object being enclosed in a moisture impermeable enclosure, a dry object to remove residual moisture from the body after initial cleansing, and an absorbent web attachable to the afflicted portion of the body to provide ongoing absorption after an initial cleansing, the absorbent web being enclosed and thus sanitarily sealed.

It is another object of the invention to provide the aforementioned wiping objects and attachable web with a moisture impermeable, flexible enclosure suitable for enclosing these components prior to use, and to enclose the same along with moisture gathered during cleansing for disposal thereof.

It is a further object of the invention to provide a sanitary kit having a thickness substantially that of the enclosed, attachable web.

Still another object of the invention is to provide a sanitary kit of limited size, considered in plan view.

Yet another object of the invention is to provide a sanitary kit which is inexpensive and readily assembled.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawing.

DETAILED DESCRIPTION OF THE PREFERRED EMBODIMENT

Figure 1:
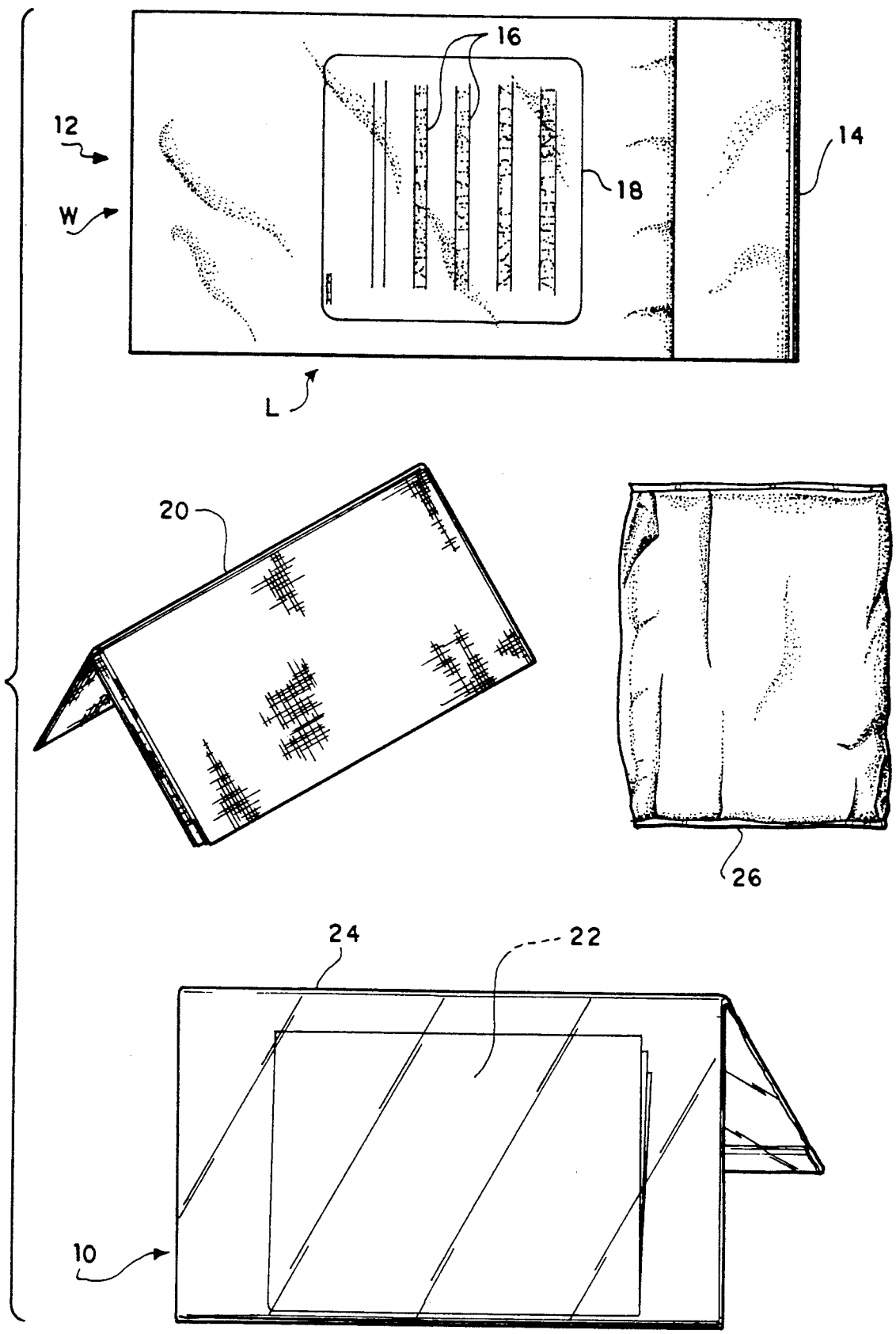
FIG. 1 is an exploded view of the components of the novel sanitary kit.

The present invention comprises a sanitary kit 10 including three components for cleansing and an enclosure maintaining the cleansing components together and excluding contaminants therefrom. The enclosure preferably comprises an envelope 12 having an open end 14, the envelope 12 being made from a thin, strong, flexible, moisture impermeable material, such as polypropylene based plastic. A portion of the envelope 12 includes indicia 16 bearing identification of the contents and instructions for a user. The indicia 16 may be printed on the envelope 12, or may be printed on a label 18 or similar sheet of material which is affixed to the envelope 12. The envelope 12 has length L and width W of 20 cm and 10 cm, respectively, or less, thus enabling the sanitary kit 10 to be carried unobtrusively in a woman's purse (not shown).

The cleansing components of the sanitary kit 10 include a dry wiping object 20, preferably comprising a section of flexible and absorbent web, such as paper towel, and a moistened wiping object 22. The moistened wiping object 22 is preferably also a paper towel, enclosed in a moisture impermeable wrapping 24. This wrapping 24 maintains the moistened wiping object 22 moist, and prevents moisture from contaminating the dry wiping object 20. Paper towels serve well as wiping objects 20 or 22 since they can be folded to be highly compact, they absorb and retain moisture well, and are inexpensive.

A sanitary napkin 26 is included in the sanitary kit 10 for application on an afflicted area of the body (not shown) after initial cleansing, the sanitary napkin 26 absorbing subsequent discharge. The sanitary napkin 26 is individually wrapped and sealed to remain sanitary, and is readily available in this form.

The wiping objects 20,22 have only minor thickness, and thus add little to the overall thickness, which is determined in large part by the sanitary napkin 26. The wiping objects 20,22 and sanitary napkin 26 are of length and width considerably less than that of envelope 12, so that they are readily placed in envelope 12 after use.

Thus a highly practical sanitary kit 10 is assembled, the wiping objects 20,22 and sanitary napkin 26 being enclosed in the envelope 12 for storage, portage, and subsequent disposal. The sanitary kit 10 is inexpensive and compact, and is readily concealed and ported.

Figure 2:
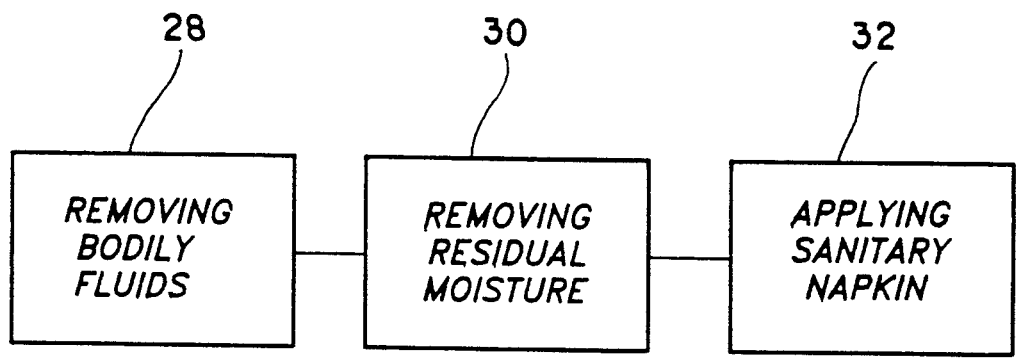
FIG. 2 is a block diagram showing the steps of using the novel sanitary kit, reading from left to right.

A method of using the sanitary kit 10, illustrated in FIG. 2 (reading left to right), comprises substantially removing bodily fluids from the outside of the body with the moistened wiping object 28, removing residual moisture from the body with the dry wiping object 30, and applying the sanitary napkin on the body 32.

It is to be understood that the present invention is not limited to the sole embodiment described above, but encompasses any and all embodiments within the scope of the following claims.

I claim:

1. A sanitary kit comprising:
   a dry wiping object,
   a wet wiping object having a moisture impermeable wrapping,
   an individually wrapped and sealed sanitary napkin, and
   an enclosure containing said objects and said wrapped and sealed sanitary napkin, said enclosure comprising an envelope having one end open, the envelope being made from a thin, strong, flexible, moisture impermeable material, a portion of the envelope bearing indicia indicating identification of the contents and instructions for a user, said envelope having length and width of 20 cm and 10 cm, respectively, said sanitary kit thereby being carried unobtrusively in a woman's purse, whereby said sanitary kit is usable to cleanse a sudden discharge of bodily fluids by removing the bodily fluids with said wet wiping object, removing residual moisture from the body with said dry wiping object, and protecting the body from subsequent discharge by applying said sanitary napkin.

2. A method of using the sanitary kit of claim 1, comprising the steps of:
   a) removing bodily fluids discharged from a person's body with the wet wiping object;
   b) removing residual moisture from a person's body with the dry wiping object, and
   c) applying the sanitary napkin, thereby protecting the body from subsequent discharge of bodily fluids.

* * * * *